United States Patent [19]
Fine

[11] Patent Number: 5,094,841
[45] Date of Patent: Mar. 10, 1992

[54] GEL FOR OPTIMUM RELEASE OF FLUORIDE WITH ANTIBACTERIAL CAPABILITY FOR USE IN THE PREVENTION OF CARIES OF ROOT SURFACE

[75] Inventor: Daniel H. Fine, Leonia, N.J.

[73] Assignee: The Trustees of Columbia University in the City of New York, New York, N.Y.

[21] Appl. No.: 214,755

[22] Filed: Jul. 5, 1988

[51] Int. Cl.$^5$ ............................................. A61K 7/18
[52] U.S. Cl. ........................................ 424/52; 424/49; 424/422; 424/426; 424/435
[58] Field of Search ................... 424/49, 52, 422, 426, 424/435

[56] References Cited

U.S. PATENT DOCUMENTS

| | | | |
|---|---|---|---|
| 3,929,988 | 12/1975 | Barth | 424/49 |
| 3,957,964 | 5/1976 | Grimm, III | 424/49 |
| 4,175,326 | 11/1979 | Goodson | 424/435 |
| 4,459,307 | 7/1984 | McHugh | 424/49 |

*Primary Examiner*—Thurman K. Page
*Assistant Examiner*—P. L. Prater
*Attorney, Agent, or Firm*—John P. White

[57] ABSTRACT

The present invention concerns a gel composition useful for treating or preventing caries of the root which comprises sodium fluoride and an antibacterial agent in concentrations sufficient to retard or prevent caries of the root and a gel carrier. In the most preferred embodiment, the gel composition further comprises preservatives and taste agents and contains a gel carrier which comprises a combination of gum tragacanth, gum arabic and agar-agar.

26 Claims, 10 Drawing Sheets

GEL FOR OPTIMUM RELEASE OF FLUORIDE WITH ANTIBACTERIAL CAPABILITY FOR USE IN THE PREVENTION OF CARIES OF ROOT SURFACE

BACKGROUND OF THE INVENTION

Topical oral medication for the prevention of dental caries has been the subject of scientific investigation since about 1940. With the advent of topical fluorides, the interest in the use of dentifrices for the prevention of dental caries has increased. Studies involving dentifrices containing approximately 0.76% sodium monofluorophosphate, $Na_2PFO_3$, as the active ingredient (e.g. Colgate ® with MFP and Macleans Fluoride ®) has established that dentifrices can be effective in helping to prevent caries (Accepted Dental Therapeutics, 37th ed., 1977, pp. 302–304). Similar studies for dentifrices containing about 0.4% stannous fluoride ($SnF_2$), e.g. Crest ® and Aim ®, have produced results in the same general range.

Sodium fluoride is also known to be effective for the prevention of dental caries but not to the same degree of effectiveness as sodium monofluorophosphate or stannous fluoride. The present invention unexpectedly reveals that sodium fluoride when use in a gel composition and in combination with an antibacterial agent prevents or treats caries of tooth roots significantly better than gels containing sodium monofluorophosphate or stannous fluoride.

SUMMARY OF THE INVENTION

The present invention concerns a gel composition useful for treating or preventing caries of the root which comprises sodium fluoride and an antibacterial agent in concentrations sufficient to retard or prevent caries of the root and a gel carrier. In the most preferred embodiment, the gel composition further comprises preservatives and taste agents and contains a gel carrier which comprises a combination of gum tragacanth, gum arabic and agar-agar.

The invention also provides a method for the prevention or treatment of caries of tooth root which comprises applying directly to the surface of the tooth root an effective amount of the composition of the present invention.

DETAILED DESCRIPTION OF THE INVENTION

Figure 1:
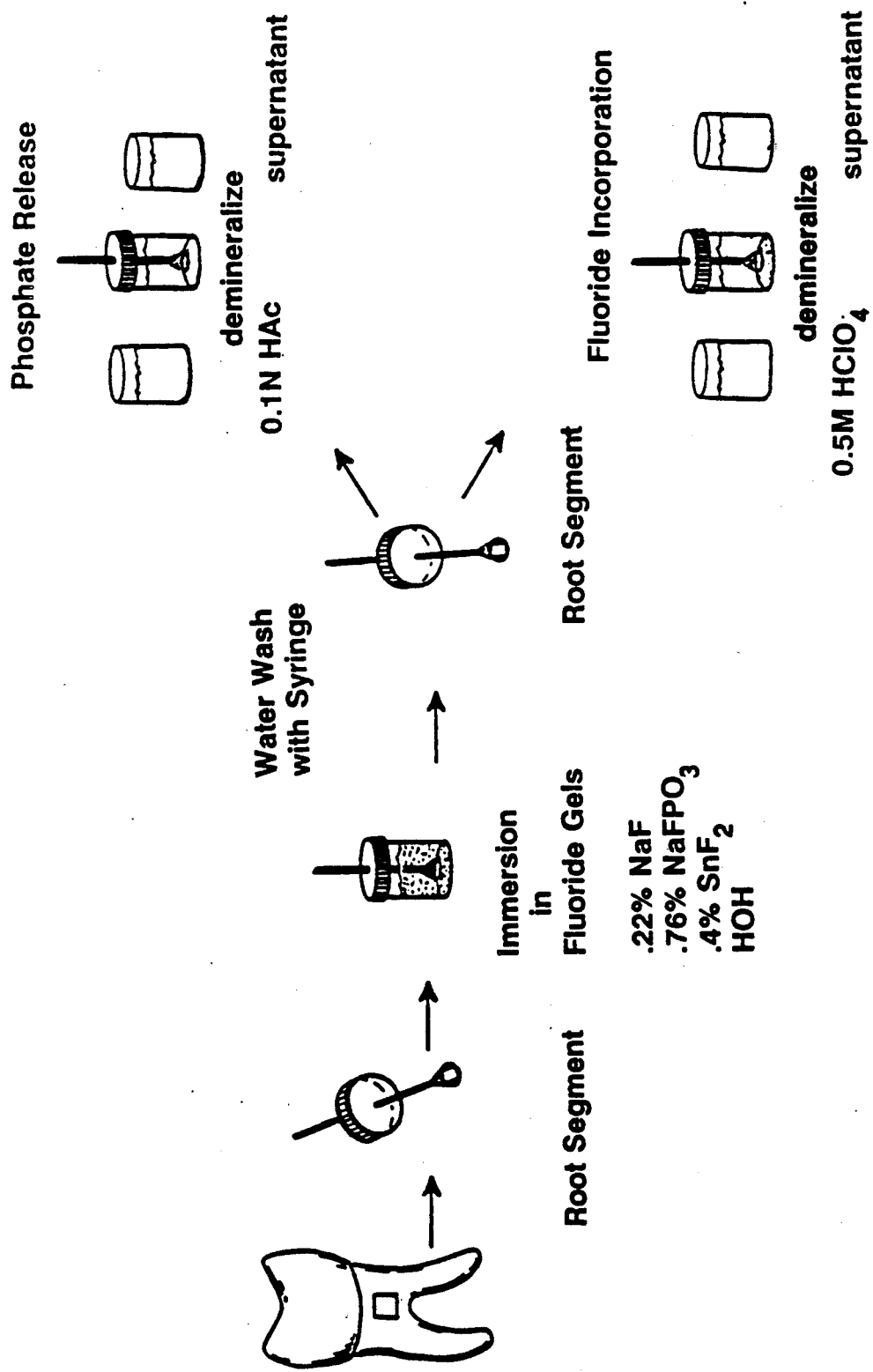
FIG. 1 illustrates the protocol for fluoride incorporation and phosphate release.

The present invention provides a gel composition useful for treating or preventing caries of tooth root which comprises sodium fluoride and an antibacterial agent in concentrations sufficient to retard or prevent caries of the root and a gel carrier.

The combination of sodium fluoride and the antibacterial agent at specific concentrations in a gelling matrix provide superior fluoride release to the tooth root and antibacterial effect against caries-producing microorganisms that attach to the tooth surface.

The fluoride of the present invention, sodium fluoride, was unexpectedly found to be superior to monofluorophosphate and stannous fluoride when used at equimolar concentrations in a gel composition. The gelling agents suitable for use in the present invention include: gelatin, carboxymethlycellulose, polyethylene gylcol, and different combinations and concentrations of agar-agar, gum arabic and gum tragacanth. It has been found that a combination of gum tragacanth, gum arabic and agar-agar is particularly useful for producing a gel which is effective for the treatment and prevention of caries of the root.

A number of preservatives, taste agents and antibacterial agents may also be added to the gel composition. Suitable preservatives, taste agents and antibacterial agents are known to those skilled in the art and can be selected based on their compatibility with the sodium fluoride and gelling agents. The antibacterial agent is defined here as any agent which is capable of killing *streptococcus sangius, Streptococcus mutans, Actinomyces viscosus,* and other bacteria associated with tooth root caries. For example, benzol-konium chloride, phenol, stannous flouride, sodium phenolate, sodium lauryl sulfate, sodium N-lauroyl sarcosinate, or sodium cocomonoglyceride sulfonate may be used in the present invention for their antibacterial and/or detergent properties. In the preferred embodiments of the invention, sodium lauryl sulfate is used as the antibacterial agent in a concentrations of 0.05 to 1.75 grams per 100 mls. of the composition. Especially useful concentrations of sodium lauryl sulfate have been found to be those between 0.05 and 0.25 grams per 100 mls. of composition.

Suitable preservatives include sodium benzoate, ascorbic acid, sorbic acid, BHA, BHT, disodium EDTA, and various parabens, such as methyl paraben, propyl paraben, butyl paraben and heptyl paraben. Numerous other preservatives generally used in tooth pastes, mouthwashes and foods may also be used in the practice of the subject invention. To date, a combination of methyl paraben and propyl paraben has been found to be a preferred preservative. Likewise, a wide variety of taste agents generally used in tooth pastes and foods may also be used in the gel composition of the present invention. In a preferred embodiment, vanillin is used as taste agent and unexpectedly has been found to contribute to the antibacterial activity of the gel composition.

The concentrations of the individual ingredients of the gel composition may vary depending on whether the gel is used for treatment of caries or prevention of caries of the root. Generally, the concentrations of sodium fluoride and the antibacterial agent will be greater in gels used for treatment than in gels used for prevention of caries of tooth root. For example, the preferred concentrations of sodium fluoride in gels for the prevention of caries of tooth root may be as low as 0.11 grams per 100 mls. of composition and preferably about 0.22 grams per 100 mls. In contrast, gels used for the treatment of caries of the root may have sodium fluoride concentrations ten times greater than those of gels for prevention, i.e. about 2.2 grams per 100 mls. of composition. In addition, it is important for the gel to have substantivity to tissue and tooth surfaces and to possess the appropriate consistency for local delivery to the tooth surface.

The most preferred gel compositions are as follows:

| CHEMICAL COMPOUND | per 100 mls | |
|---|---|---|
| | CONCENTRATION | PREFERRED CONCENTRATION RANGE |
| (1) Sodium fluoride | .22 g | .11–2.20 g |
| (2) Sodium lauryl sulfate | .11 g | .05–1.75 g |
| (3) Vanillin | .50 g | .25–.65 g |
| (4) Paraben (methyl) | .10 g | .05–.30 |
| (5) Paraben (propyl) | .01 g | .005–.03 |
| (6) Gum tragacanth | 3.5 g | 2.0–4.0 g |
| (7) Gum arabic | 0.5 g | 0.25–2.5 g |
| (8) Agar-agar | 0.5 g | 0.25–2.0 g |

Chemicals 1–5 are added to 100 mls. of distilled deionized water that is heated to 195° F. When dissolved the gums (6–8) are added in sequence while stirring to yield a homogenous gel after cooling.

The invention also provides a method for the prevention or treatment of caries of tooth root which comprises applying directly to the surface of the tooth root an effective amount of the composition described hereinabove. Additionally, the invention concerns methods for the incorporation of fluoride into tooth root and for protecting tooth root from demineralization. These methods comprise applying directly to the surface of the tooth root an effective amount of the composition of the present invention.

Certain preferred embodiments of the invention are set forth in the Experimental Detail section which follows. This section is provided to aid in an understanding of the invention but is not intended to, and should not be contrued to, limit in any way the invention as set forth in the claims which follow thereafter.

EXPERIMENTAL DETAILS

A series of in vitro and in vivo experiments were performed establishing the usefulness and uniqueness of the present invention. A standard in vitro model system described by Fine, Wilton and Caravana, 1984 (Infection and Immunity 44:332) was used. This system utilized root segments, 4 mm×3 mm in size, 250 mm in thickness, obtained from human teeth extracted for orthodontic purposes. They were covered with nail polish leaving the cemental surface exposed and then mounted to a capillary pipette for immersion into a 2.0 ml autoanalyzer cup containing testing agents. This was done to determine which of the three commercially acceptable, over-the-counter fluorides (sodium fluoride at 0.22%; monofluorophosphate at 0.76%; and, stannous fluoride at 0.40%) was most effective in: (1) delivering fluoride to human root surfaces, (2) limiting phosphate (mineral) releases from the root surface after an acid challenge; and, (3) limiting the ingress of small low molecular weight substances into roots. The following gels were prepared:

(1) a gel containing sodium fluoride at 0.22% as described below;

| | |
|---|---|
| Sodium Fluoride | .22 g/100 mls. |
| Sodium Lauryl Sulfate | .110 g/100 mls. |
| Vanillin | .500 g/100 mls. |
| Paraben (methyl) | .100 g/100 mls. |
| Paraben (propyl) | .110 g/100 mls. |
| Gum Tragacanth | 3.5 g/100 mls. |
| Gum Arabic | 0.5 g/100 mls. |
| Agar-Agar | 0.5 g/100 mls. |

(2) a gel containing 0.76 grams of monoflourophosphate (MFP) plus all the other ingredients described above [the sodium fluoride was replaced with MFP]; and, (3) a gel containing 0.4 grams of stannous fluoride in 0.78% glycerin per 100 mls of gel.

FLUORIDE INCORPORATION INTO ROOTS

Root segments were incubated in each of the three fluoride preparations and in a water control gel for one hour at room temperature. Segments were washed, cleaned free of wax and decalcified by incubation in 0.5M perchloric acid for one hour. The solution contained in the 2 ml autoanalyzer cup was brought to pH 5.1–5.3 by addition of "adjusted TISAB". The solution was then assayed for fluoride content by means of a Fluoride Selective Electrode (Orion Co., Finland). Root segments were then washed and re-demineralized in 0.5M prechloric acid as before and one again analyzed for fluoride (FIG. 1). Results demonstrated that fluoride incorporation was best in the sodium fluoride gel and poorest in the stannous fluoride gel (see FIG. 2). The NaF gel provided almost twice as much fluoride as did $NaFPO_3$ (0.534, SE 0.52 ppm/mm$^2$ vs. 0.298, SE 0.160 ppm/mm$^2$), while both were significantly better than $SnF_2$ gel, or water ($p<0.05$).

MINERAL RELEASE AFTER AN ACID CHALLENGE

Figure 2:
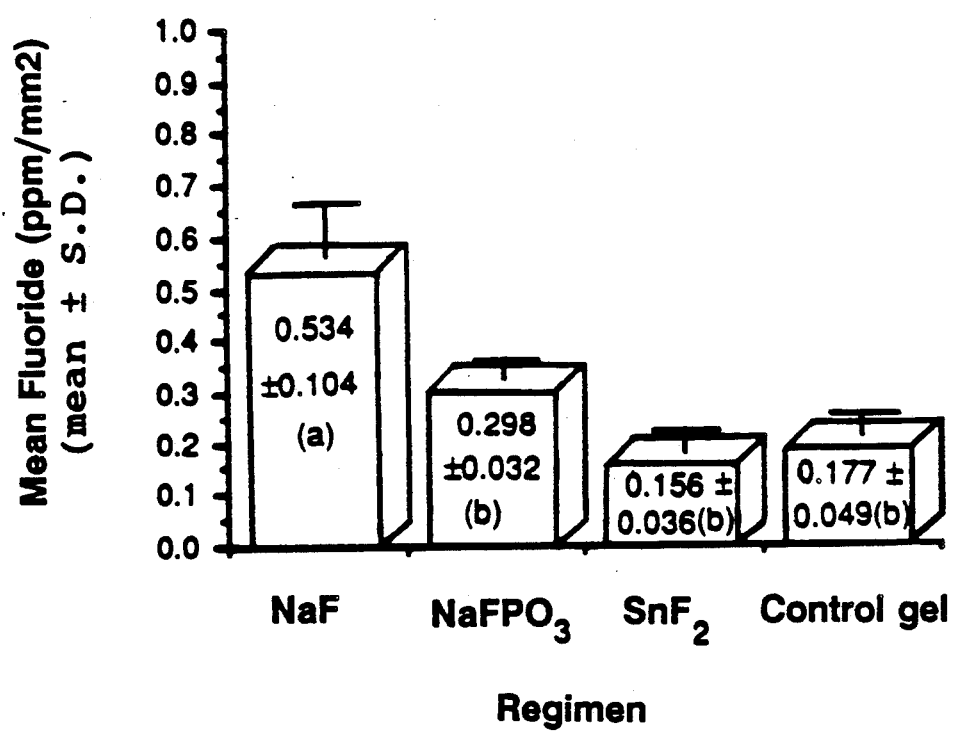
FIG. 2 is a graphical representation of the data obtained for fluoride incorporation into cementum.
Figure 3:
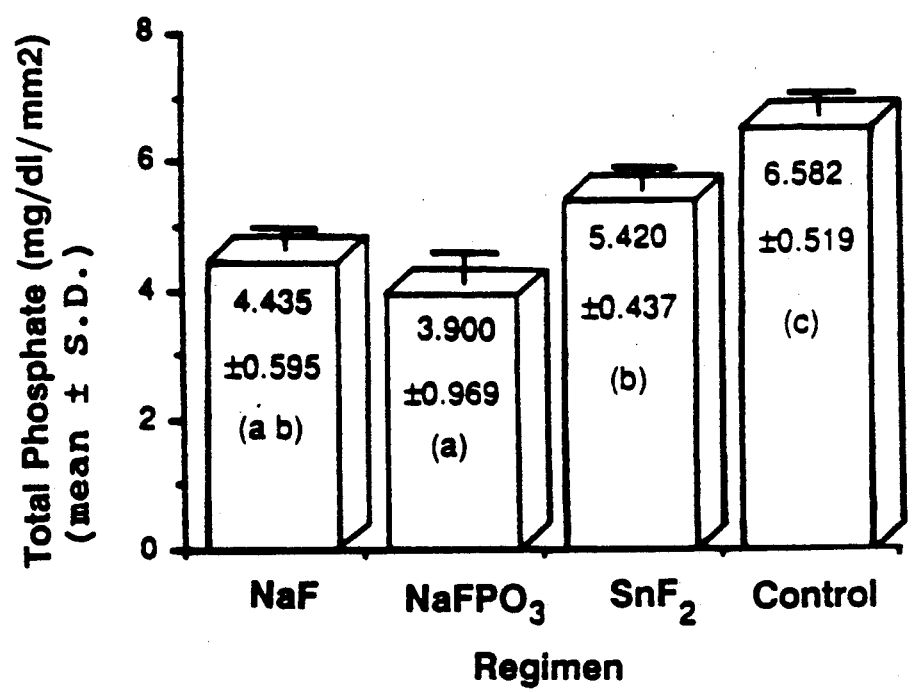
FIG. 3 is a graphical representation of the data obtained for mineral release from cementum.

Root segments were incubated in each of the three fluoride preparations and in a water control gel for one hour at room temperature, washed in water and then placed in a demineralizing solution of 0.1N acetic acid, pH 4.1 for 15 minutes at room temperature. The acetic acid solutions were analyzed for phosphate content released from the root by a standard molybdenum assay (FIG. 2). The untreated control root segments were demineralized but left untreated by fluoride (FIG. 2). Results demonstrated that both sodium fluoride and MFP were significantly better than stannous fluoride or water ($p<0.05$) at protecting the root segments from demineralization by the acid challenge (see FIG. 3).

LIMITATION OF INGRESS OF LOW MOLECULAR WEIGHT SUBSTANCES

Figure 4:
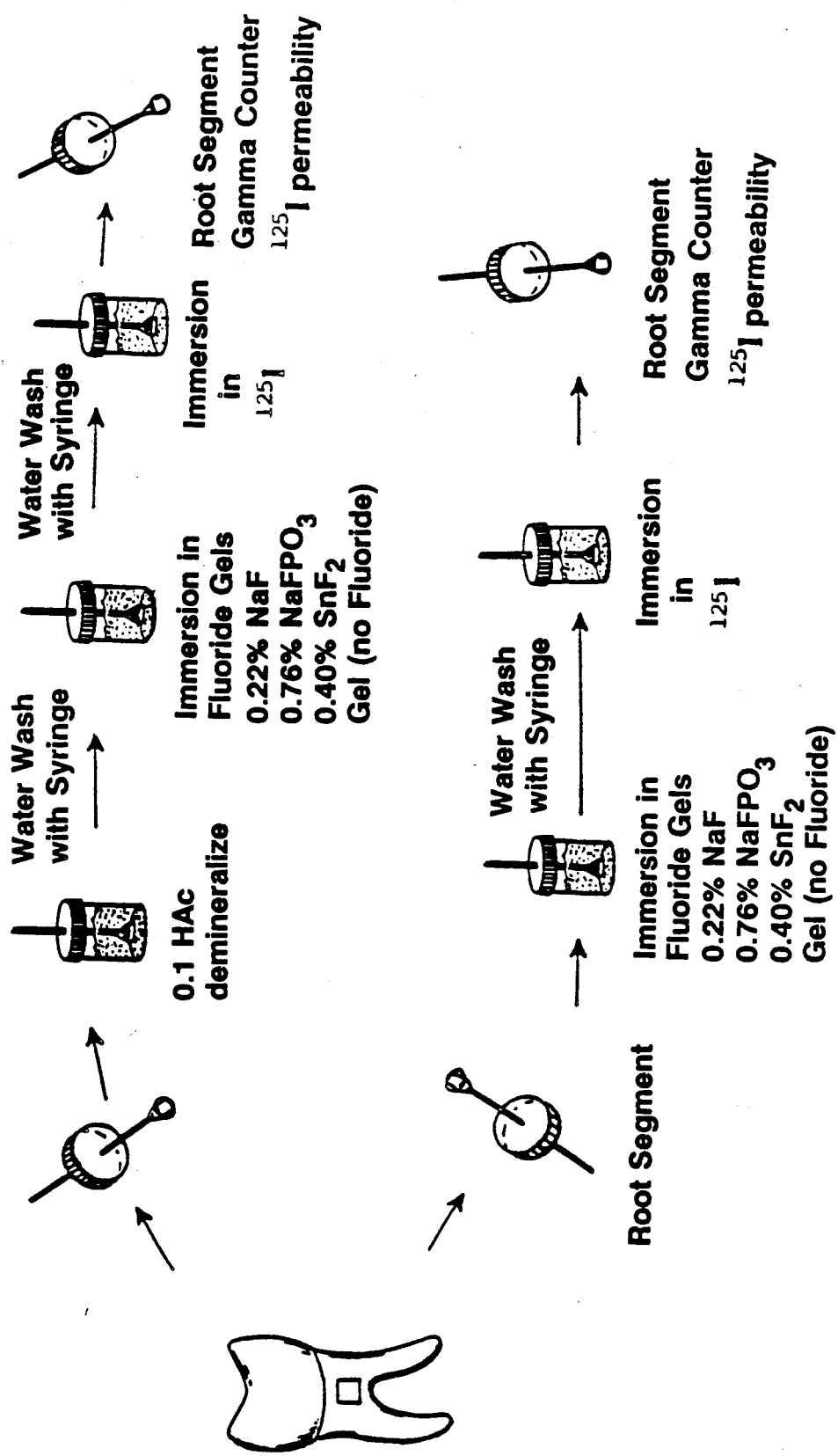
FIG. 4 illustrates the protocol for iodine permeability.
Figure 5A:
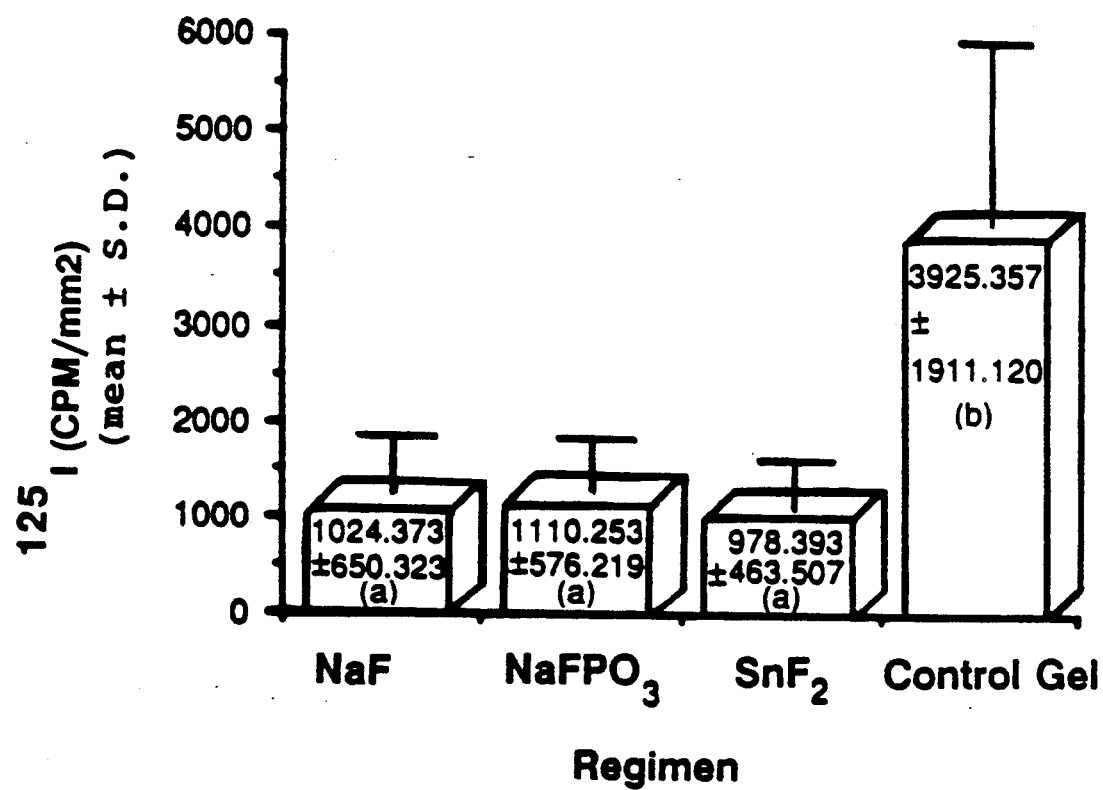
FIG. 5a is a graphical representation of the data obtained for iodine permeability of cemuntum.
Figure 5B:
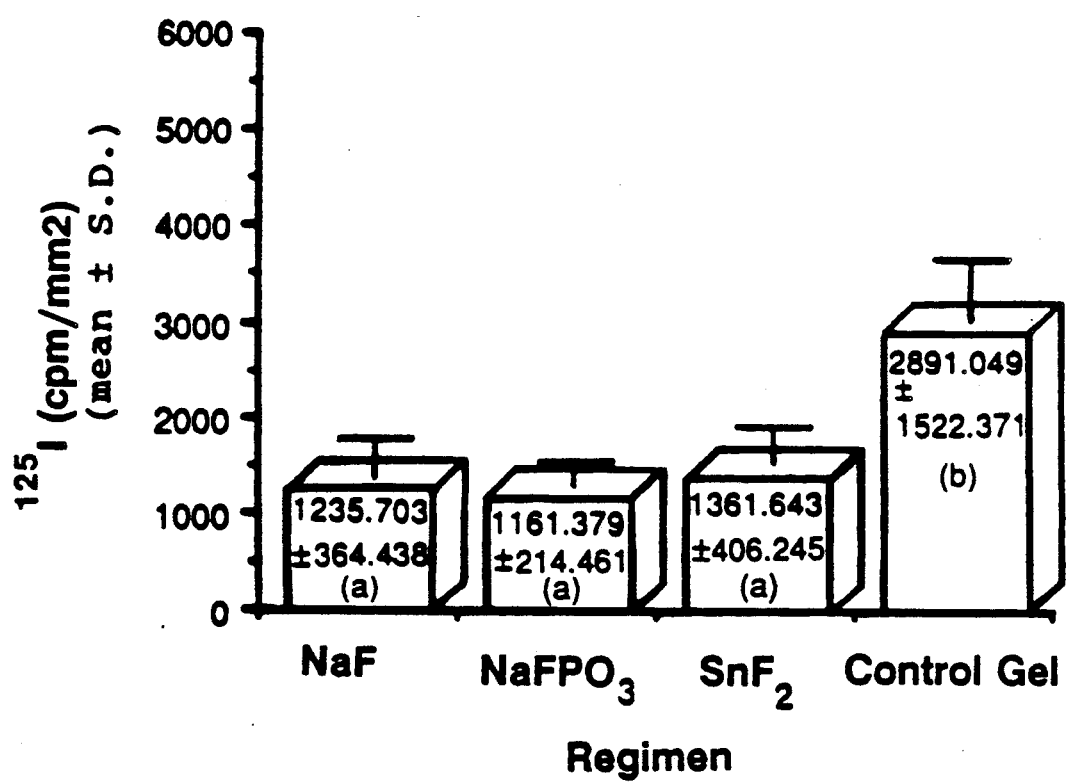
FIG. 5b is a graphical representation of the iodine permeability of cemuntum with an acid pretreatment step.

Root segments were placed in the three fluoride gels and a water control as described, with and without an acid pretreatment. Segments were then washed in water to remove the adherent gel and then placed in a solution containing 80 uCi/ml of NaI$^{125}$ in a phosphate buffer for 15 minutes at room temperature. Segments were washed, cleaned free of wax and assayed for gamma radioactivity (FIG. 4). Results indicated that each of the fluorides provided a decrease in iodide permeability as compared to the water control (FIG. 5a and FIG. 5b).

Two additional series of experiments were performed. In the first series, fluoride incorporation was analyzed in root segments that were treated with a variety of commercial fluoride preparations including: Crest ®, Colgate ®, Aim ®, Gelkam ®, and Omni ®. The sodium fluoride gel of the present invention along with the sodium fluoride gel without the antibacterial agent were included in the tests and compared to the commercial products listed above using the in vitro design described earlier. Results indicated that the sodium fluoride gel of the present invention was at least twice as effective with respect to fluoride incorporation into tooth roots as any of the gels or pastes tested excluding Crest ® (in this case sodium fluoride produced 0.486 ppm/mm and Crest ® produced 0.299 ppm/mm).

A second series of experiments analyzed the antibacterial effect of the commercial gels and pastes and compared the results to those obtained with the sodium fluoride gel of the present invention. Gels and pastes were tested for antibacterial effectiveness against several pioneer gram (+) bacteria found in dental plaque, namely, Streptococcus sangius, S. mutans and Actinomyces viscosus. A standard innoculum of an overnight culture of each of the organisms was placed into 9 mls of Trypticase Soy Beroth to which was added 1 ml of each of the following gels or pastes: (1) Crest ®, (2) Aim ®, (3) Colgate ®, (4) Omni ®, (5) GelKam ®, (6) the sodium fluoride gel of the present invention, and (7) the sodium fluoride gel without the antibacterial agent. Of the commercial products both Colgate ® and Aim ® completely inhibited growth of the test bacteria after 24 hours of incubation at 37° C. The sodium fluoride gel with the active agents also inhibited growth of all test bacteria.

To summarize, the sodium fluoride gel provided the best overall protection as compared to the other gels and pastes tested. The sodium fluoride gel performed best with respect to fluoride incorporation into roots, inhibition of phosphate release from roots and antibacterial activity against pioneer plaque microorganisms. None of the other agents tested had a comparable record.

TABLE 1

| | gel | ppm/mm$^2$ | | b | area (mm) |
|---|---|---|---|---|---|
| NaF Gel w/ oSLS | 1 | 0.486 | | 4.355 | 8.960 |
| | 2 | 0.493 | | 3.822 | 7.750 |
| | 3 | 0.383 | 0.452 | 3.214 | 8.400 |
| | 4 | 0.351 | | 3.069 | 8.750 |
| | 5 | 0.547 | | 5.358 | 9.800 |
| NaF Gel w/ SLS | 1 | 0.351 | | 4.305 | 12.250 |
| | 2 | 0.616 | | 5.916 | 9.600 |
| | 3 | 0.437 | 0.486 | 6.138 | 14.060 |
| | 4 | 0.405 | | 2.739 | 6.760 |
| | 5 | 0.623 | | 6.324 | 10.150 |
| Gel-Kam | 1 | 0.236 | | 2.056 | 8.700 |
| | 2 | 0.215 | | 1.786 | 8.320 |
| | 3 | 0.098 | 0.196 | 0.724 | 7.360 |
| | 4 | 0.253 | | 2.084 | 8.250 |
| | 5 | 0.176 | | 1.074 | 6.090 |
| Colgate | 1 | 0.160 | | 1.208 | 7.560 |
| | 2 | 0.260 | | 2.415 | 9.300 |
| | 3 | 0.085 | 0.221 | 0.793 | 9.280 |
| | 4 | 0.255 | | 2.500 | 9.800 |
| | 5 | 0.347 | | 2.472 | 7.130 |

TABLE 1-continued

| | gel | ppm/mm$^2$ | | b | area (mm) |
|---|---|---|---|---|---|
| Crest | 1 | 0.154 | | 1.535 | 9.990 |
| | 2 | 0.255 | | 1.910 | 7.480 |
| | 3 | 0.325 | 0.299 | 2.812 | 8.640 |
| | 4 | 0.436 | | 3.793 | 8.700 |
| | 5 | 0.325 | | 2.805 | 8.640 |
| Omnii | 1 | 0.260 | | 1.552 | 5.980 |
| | 2 | 0.240 | | 1.811 | 7.560 |
| | 3 | 0.081 | 0.221 | 0.728 | 8.990 |
| | 4 | 0.262 | | 2.512 | 9.570 |
| | 5 | 0.260 | | 2.037 | 7.830 |
| Aim | 1 | 0.215 | | 1.758 | 8.160 |
| | 2 | 0.150 | | 0.820 | 5.460 |
| | 3 | 0.166 | 0.175 | 1.493 | 8.990 |
| | 4 | 0.115 | | 0.834 | 7.260 |
| | 5 | 0.229 | | 2.249 | 9.800 |
| Control | 1 | 0.280 | | 2.773 | 9.900 |
| | 2 | 0.149 | | 2.009 | 13.500 |
| | 3 | 0.375 | 0.244 | 2.812 | 7.500 |
| | 4 | 0.201 | | 1.791 | 8.910 |
| | 5 | 0.214 | | 1.875 | 8.750 |

IN VIVO EXPERIMENTS

Two in vivo experiments utilizing a Latin square design were performed. The first experiment was performed at Columbia University using five adults with a history of coronal caries and consisted of a 5×5 Latin square, each subject having only one treatment for one week. The second experiment was performed at the University of Pennsylvania using ten adults with a similar coronal caries history and consisted of two 5×5 Latin squares. In all a total of fifteen patients participated in the studies. In both experiments two segments 2 mm×5 mm×250 μm in thickness were fashioned from roots obtained from orthodontic patients and were fastened interproximally between two posterior teeth of each of the participants for five one week periods. In each of four weeks the patients were instructed to apply a different agent (toothpaste without fluoride, toothpaste with fluoride [Crest], the gel of the present invention as described above with 0.22% NaF, and the gel of the present invention substituting NaF with MFP) to each of the two strips contained in their mouths. The fifth week the patient was instructed to abstain from all toothcleaning procedures. Root strips obtained from the volunteers who were in the study conducted at Columbia were used to gather information about bacterial penetration, which was determined by examination of stained serial sections under a light microscope, and phosphate release as a measure of demineralization. Root strips obtained in the Pennsylvania experiment were used to obtain information about phosphate release and fluoride incorporation into roots.

Figure 6:
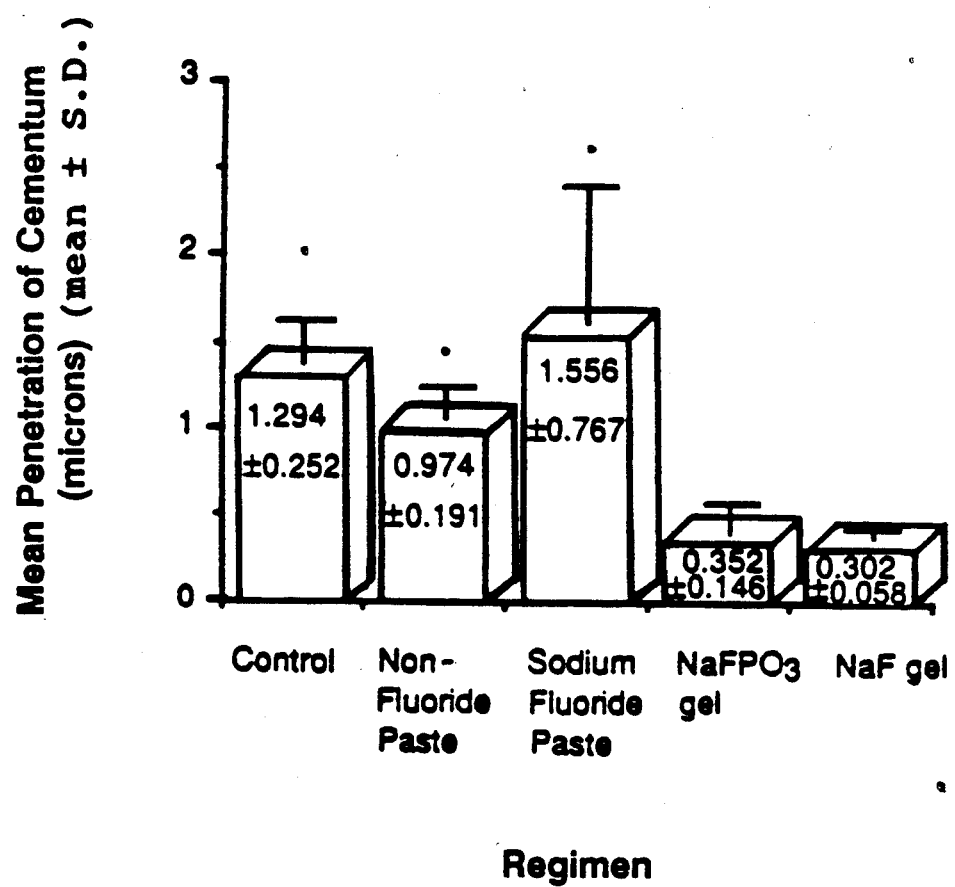
FIG. 6 is a graphical representation of the in vivo data obtained for bacterial penetration of cemuntum.
Figure 7:
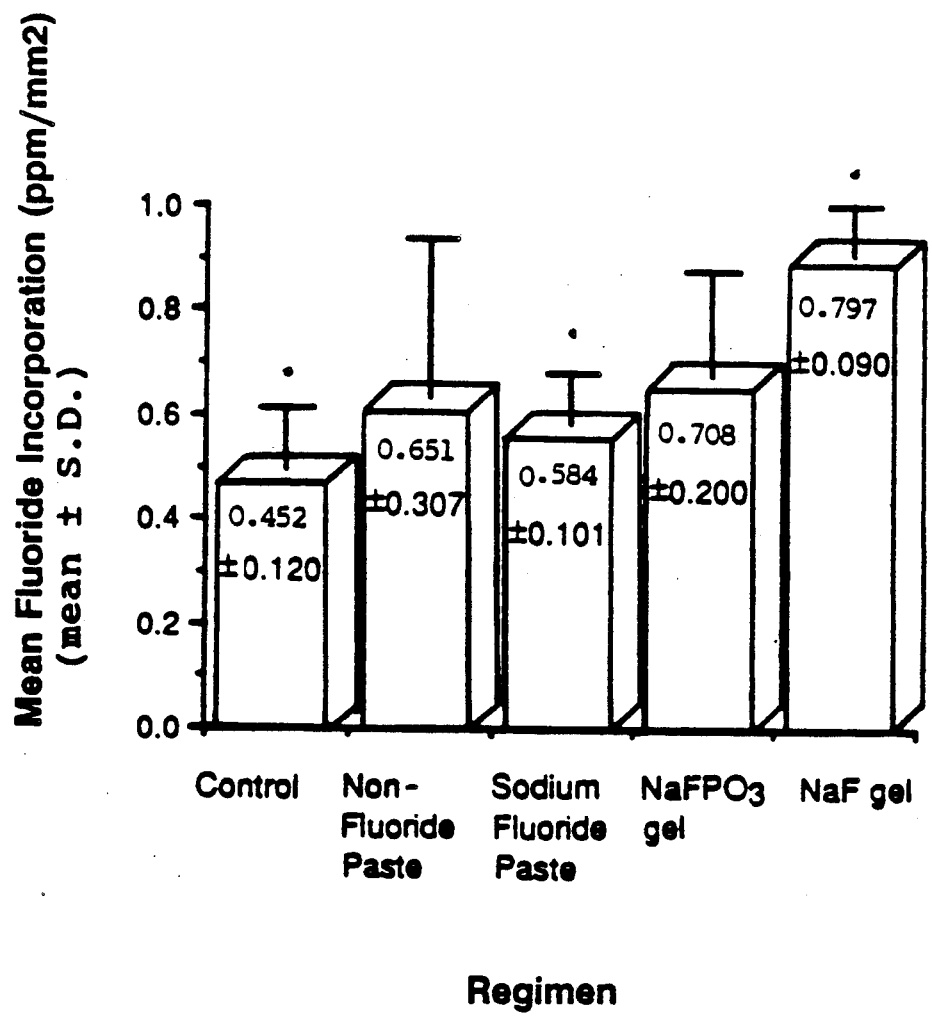
FIG. 7 is a graphical representation of the in vivo data obtained for fluoride incorporation.
Figure 8A:
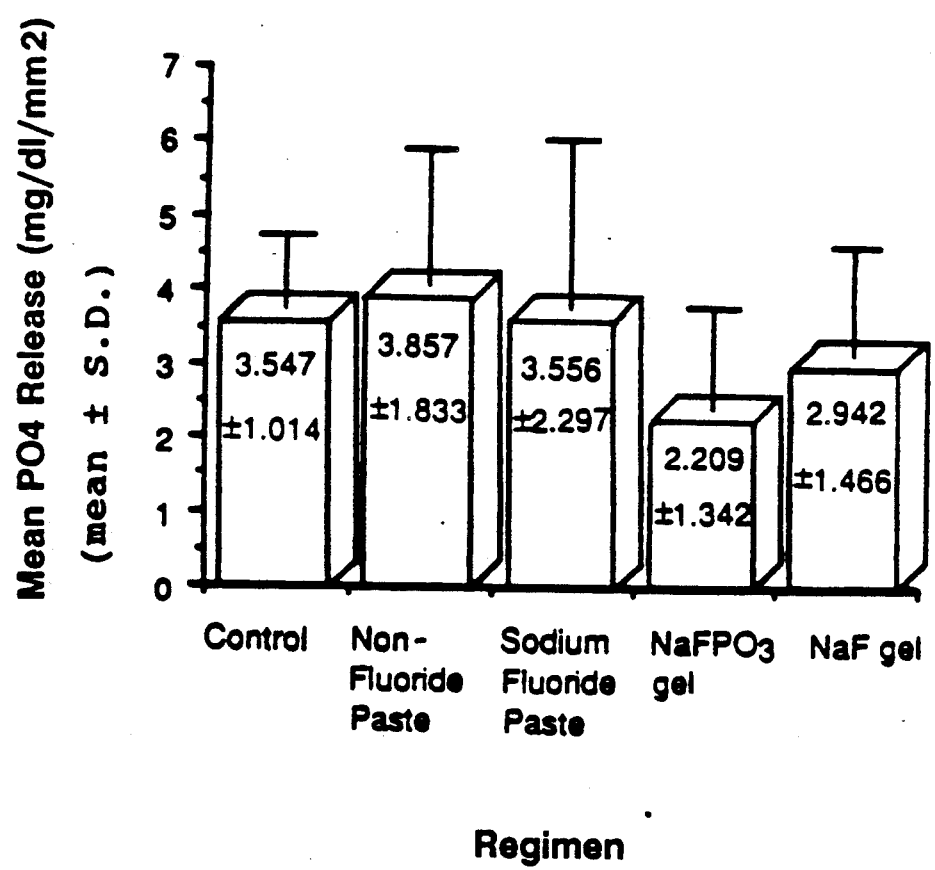
FIGS. 8a and 8b are graphical representations of the in vivo data obtained for phosphate release.
Figure 8B:
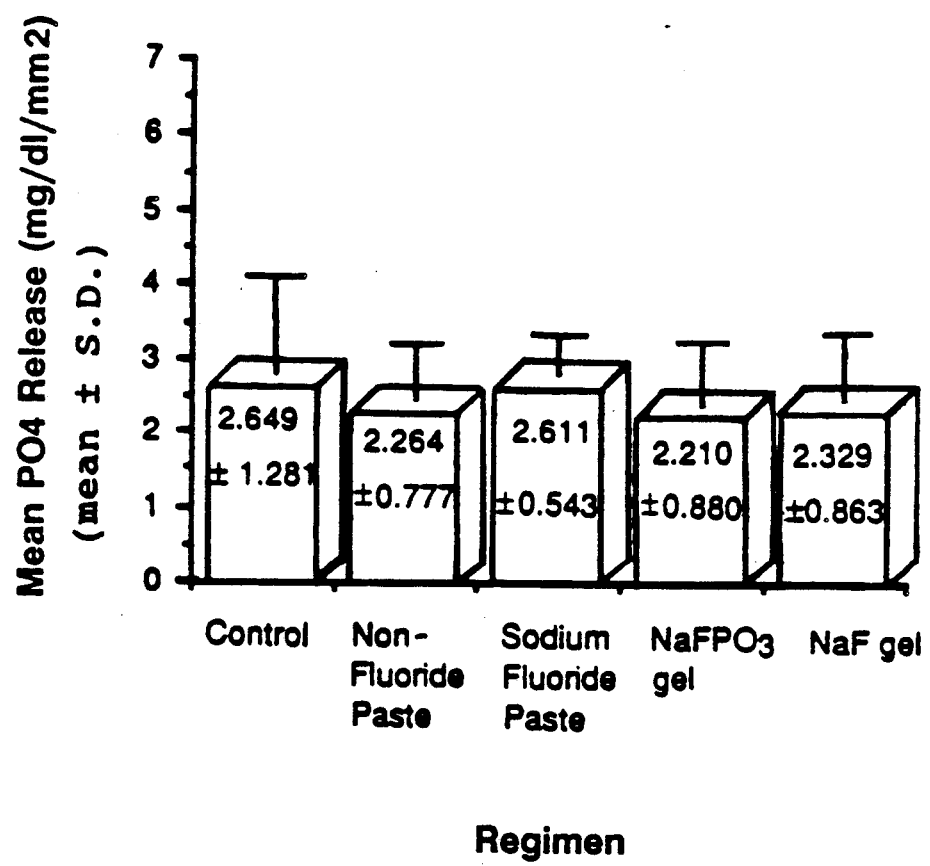

The NaF gel (3.2 mu) was statistically significantly better than all other treatments (12.94, 9.74, 15.56, except NaFPO$_3$ gel 3.52) at the 0.5 confidence level in inhibiting microbial penetration, and was statistically significantly better than treatments 1 and 3 at the 0.1 confidence level. (FIG. 6). The NaF gel had statistically significantly more flouride ion uptake (0.797 ppm/mm$^2$) than treatments 1 (0.452), 2(0.651), and 3(0.584) at the 0.10 confidence level, and than treatments 1 and 3 at the 0.5 confidence level. The NaF gel ranked better than the NaFPO$_3$ gel (0.708), but the differences were not statistically significant (FIG. 7). MFP and NaF were also superior to the other gels or pastes in limitation of phosphate release but these results were not statistically significant (see FIG. 8a and FIG. 8b).

The second series of experiments demonstrated a similar trend but once again statistical differences were not achieved. However, data on fluoride uptake indicated a highly significant difference between the NaF gel and the non-brushing regimen. Differences between the NaF group and the toothpaste groups with and without fluoride also demonstrated a profound superiority for the NaF gel of the present invention.

What is claimed is:

1. A gel composition useful for treating or preventing caries of tooth root which consists essentially of from about 0.11 to about 2.20 grams per 100 mls of the composition of sodium fluoride and a sufficient concentration of an antibacterial agent such that the composition retards or prevents caries of the root and a gel carrier.

2. A composition of claim 1, wherein the gel carrier comprises a plurality of gelling agents.

3. A composition of claim 1, wherein the gel carrier is selected from the group consisting of gelatin, carboxymethylcellulose, polyethylene glycol, agar-agar, gum arabic, gum tragacanth, and combinations thereof.

4. A composition of claim 1, wherein the gel carrier comprises gum tragacanth, gum arabic and agar-agar.

5. A composition of claim 4, wherein the gel carrier comprises per 100 mls of composition 2.0 to 4.0 grams of gum tragacanth, 0.5 to 2.5 grams of gum arabic, and 0.5 to 2.0 grams of agar-agar.

6. A composition of claim 1, wherein the antibacterial agent is sodium lauryl sulfate.

7. A composition of claim 6, wherein the concentration of sodium lauryl sulfate is about 0.05 to about 1.75 grams per 100 mls. of the composition.

8. A composition of claim 7, wherein the concentration of sodium lauryl sulfate is about 0.05 to about 0.25 grams per 100 mls. of the composition.

9. A composition of claim 8, wherein the concentration of sodium lauryl sulfate is about 0.10 grams per 100 mls. of the composition.

10. A composition of claim 1, wherein the concentration of sodium fluoride is about 0.22 grams per 100 mls. of the composition.

11. A composition of claim 1 further comprising a preservative.

12. A composition of claim 11, wherein the preservative is selected from the group consisting of sodium benzoate, BHA, BHT, disodium EDTA, methylparaben, propylparaben, heptylparaben, ascorbic acid, sorbic acid and combinations thereof.

13. A composition of claim 12, wherein the preservative is a combination of methylparaben and propylparaben.

14. A composition of claim 1 further comprising a taste agent.

15. A composition of claim 14, wherein the taste agent is vanillin.

16. A gel composition for the treatment or prevention of caries of tooth root consisting essentially of about 0.11 to about 2.2 grams sodium fluoride, about 0.05 to about 1.75 grams sodium lauryl sulfate, about 0.25 to about 0.65 grams vanillin, about 0.05 to about 0.30 grams methylparaben, about 0.005 to about 0.03 grams propylparaben, about 2.0 to about 4.0 grams gum tragacanth, about 0.25 to about 2.5 grams gum arabic, and about 0.25 to about 2.0 grams agar-agar per 100 mls. of composition.

17. A gel composition for the treatment or prevention of caries of tooth roots consisting essentially of about 0.22 grams sodium fluoride, about 0.10 grams sodium lauryl sulfate, about 0.50 grams vanillin, about 0.10 grams methylparaben, about 0.01 grams propylparaben, about 3.50 grams gum tragacanth, about 0.5 grams gum arabic, and about 0.50 grams agar-agar per 100 mls. of composition.

18. A method for the prevention or treatment of caries of tooth root which comprises applying directly to the surface of the tooth root an effective amount of the composition of claim 1 for said prevention or treatment.

19. A method for the prevention or treatment of caries of tooth root which comprises applying directly to the surface of the tooth root an effective amount of the composition of claim 16 for said prevention or treatment.

20. A method for the prevention or treatment of caries of tooth root which comprises applying directly to the surface of the tooth root an effective amount of the composition of claim 17 for said prevention or treatment.

21. A method of incorporating flouride into tooth root which comprises applying directly to the surface of the tooth root an effective amount of the composition of claim 1 for said prevention or treatment.

22. A method of incorporating flouride into tooth root which comprises applying directly to the surface of the tooth root an effective amount of the composition of claim 16 for said prevention or treatment.

23. A method of incorporating flouride into tooth root which comprises applying directly to the surface of the tooth root an effective amount of the composition of claim 17 for said prevention or treatment.

24. A method of protecting tooth root from demineralization which comprises applying directly to the surface of the tooth root an effective amount of the composition of claim 1 for said prevention or treatment.

25. A method of protecting tooth root from demineralization which comprises applying directly to the surface of the tooth root an effective amount of the composition of claim 16 for said prevention or treatment.

26. A method of protecting tooth root from demineralization which comprises applying directly to the surface of the tooth root an effective amount of the composition of claim 17 for said prevention or treatment.

* * * * *